United States Patent
Adhikarath Balan et al.

(10) Patent No.: US 12,232,697 B2
(45) Date of Patent: *Feb. 25, 2025

(54) OVER THE SCOPE CLIP WITH REPOSITIONAL CAPABILITY

(71) Applicants: BOSTON SCIENTIFIC MEDICAL DEVICE LIMITED, Galway (IE); BOSTON SCIENTIFIC SCIMED, INC., Maple Grove, MN (US)

(72) Inventors: Arun Adhikarath Balan, Aluva (IN); Rajivkumar Singh, Thane (IN); Deepak Kumar Sharma, Muzaffarnagar (IN); Paul Smith, Smithfield, RI (US)

(73) Assignees: Boston Scientific Medical Device Limited, Galway (IE); Boston Scientific Scimed, Inc, Maple Grove, MN (US)

( * ) Notice: Subject to any disclaimer, the term of this patent is extended or adjusted under 35 U.S.C. 154(b) by 389 days.

This patent is subject to a terminal disclaimer.

(21) Appl. No.: 17/806,624

(22) Filed: Jun. 13, 2022

(65) Prior Publication Data
US 2023/0027249 A1     Jan. 26, 2023

Related U.S. Application Data

(60) Provisional application No. 63/203,384, filed on Jul. 20, 2021.

(51) Int. Cl.
*A61B 1/00*     (2006.01)
*A61B 1/005*     (2006.01)
(Continued)

(52) U.S. Cl.
CPC ........ *A61B 1/0014* (2013.01); *A61B 1/00135* (2013.01); *A61B 1/005* (2013.01);
(Continued)

(58) Field of Classification Search
CPC ..... A61B 1/00131–0014; A61B 17/122–1285; A61B 2017/1225
See application file for complete search history.

(56) References Cited

U.S. PATENT DOCUMENTS

| 8,685,043 B2 | 4/2014 | Jugenheimer et al. |
| 9,980,713 B2 | 5/2018 | Arongalt et al. |

(Continued)

*Primary Examiner* — Elizabeth Houston
*Assistant Examiner* — Jonathan A Hollm
(74) *Attorney, Agent, or Firm* — Fay Kaplun & Marcin, LLP

(57) ABSTRACT

A clipping system includes a cap configured to be mounted over a distal end of an endoscope. A clip mountable over the cap to move between an insertion configuration, in which first and second jaws extend over opposing portions of the cap so that the first and second jaws are separated from one another, a review configuration, in which the clip is moved distally relative to the cap so that a portion of the clip extends distally until at least a portion of the clip extends into a field of view of the optical system of an endoscope on which the cap is mounted, and a deployed configuration in which the clip is moved distally off of the clip so that the first and second jaws are drawn toward one another under the bias of the at least one hinge to close over tissue received therebetween.

15 Claims, 8 Drawing Sheets

(51) Int. Cl.
*A61B 17/122* (2006.01)
*A61B 17/128* (2006.01)
*A61B 17/00* (2006.01)

(52) U.S. Cl.
CPC ...... *A61B 17/1227* (2013.01); *A61B 17/1285* (2013.01); *A61B 2017/00296* (2013.01); *A61B 2217/005* (2013.01)

(56) References Cited

U.S. PATENT DOCUMENTS

| | | |
|---|---|---|
| 11,013,518 B2 | 5/2021 | Zhong et al. |
| 2011/0208210 A1* | 8/2011 | Baur ................ A61B 18/14 606/142 |
| 2020/0375583 A1 | 12/2020 | Congdon et al. |
| 2020/0397445 A1* | 12/2020 | Shikhman ........... A61B 17/083 |
| 2021/0052141 A1 | 2/2021 | Schurr et al. |
| 2021/0059677 A1* | 3/2021 | Jin ................... A61B 17/122 |

* cited by examiner

OVER THE SCOPE CLIP WITH REPOSITIONAL CAPABILITY

PRIORITY CLAIM

The present disclosure claims priority to U.S. Provisional Patent Application Ser. No. 63/203,384 filed Jul. 20, 2021; the disclosure of which is incorporated herewith by reference.

FIELD

The present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, entering the body via the GI tract and penetrating tissue to exit the GI tract to operate on tissue outside the GI tract, and endoscopic treatment/repair of post-surgical issues (e.g., post-surgical leaks, breakdown of surgical staple lines, and anastomotic leaks).

Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient. In some cases, however, current endoscopic closure devices may be difficult to use, time consuming to position, or insufficient for certain perforations, conditions and anatomies. For example, current over-the-scope clips generally require launching of the clip from a position in which the clip itself is not visible to the operator. That is, prior to clipping the operator may view the target tissue to be clipped and, based on this visualization of the target tissue may determine that the distal end of the device and the clip are in a desired position relative to the target tissue. Based on the observation of the target tissue, the operator then deploys the clip without being able to see the clip itself until it is deployed.

SUMMARY

The present embodiments are directed to a clipping system for treating tissue, comprising a cap configured to be mounted over a distal end of an endoscope, the cap extending longitudinally from a proximal end to a distal end and including a channel extending therethrough so that the cap may be located adjacent to target tissue within a living body. A clip is configured to be mounted over the cap, the clip including first and second jaws movably connected to one another via hinges, at least one of the hinges being biased to draw the first and second jaws toward one another. The clip is movable relative to the cap between an insertion configuration, in which the first and second jaws extend over opposing portions of the cap so that the first and second jaws are separated from one another to receive a target tissue therebetween, a review configuration, in which the clip is moved distally relative to the cap so that a portion of the clip extends distally until at least a portion of the clip extends into a field of view of the optical system of an endoscope on which the cap is mounted, and a deployed configuration in which the clip is moved distally off of the clip so that the first and second jaws are drawn toward one another under the bias of the at least one hinge to close over tissue received therebetween. A deployment element extends from a distal end releasably coupled to the clip through the channel of the cap to a proximal end which, in use, remains outside the living body while the cap is adjacent to the target tissue, the deployment element being configured so that a proximal movement of the deployment element relative to the cap moves the clip distally relative to the cap toward the deployed configuration. A repositioning element extends from a distal end coupled to one of the cap and the clip proximally through the channel of the cap to a proximal end that, in use, remains outside the living body, the repositioning element being configured so that moving the repositioning element proximally relative to the cap moves the clip proximally relative to the cap from the review configuring to the insertion configuration.

In an embodiment, a distal portion of the deployment element may be looped about the first jaw of the clip such that a portion of the distal portion of the deployment element is crimped between an interior surface of the cap and an exterior surface of an endoscope on which the cap is mounted, wherein an enlargement at the distal end of the deployment element may be engaged between adjacent teeth of the first jaw, a remaining length of the deployment element extending proximally from the clip to be received enter a distal opening of the endoscope on which the cap is mounted to extend proximally through a channel of the endoscope.

In an embodiment, the cap may be formed of a transparent material and may be configured to fit over the distal end of an endoscope via a friction fit so that a proximal portion of the cap extends over the distal end of an endoscope on which the cap is mounted and a distal portion of the cap extends distally past the distal end of the endoscope.

In an embodiment, in the insertion configuration the clip may extend over the proximal portion of the cap and, in the review configuration the clip may extend over the distal portion of the cap so that the clip is visible via an optical system of an endoscope on which the cap is mounted through the transparent cap.

In an embodiment, the cap may include a protrusion extending from an exterior surface of the cap, the protrusion configured to engage a portion of the clip when the clip is in the review configuration.

In an embodiment, the distal end of the repositioning element may releasably engage the second jaw of the clip, a remaining length of the repositioning element passing through a longitudinal slot extending through the cap to extend proximally through a channel of an endoscope on which the cap is mounted.

In an embodiment, the system may further comprise a biasing element extending between a distal end of the cap and a stop at the distal-most end of an endoscope on which the cap is mounted, the biasing element biasing the cap toward the insertion configuration, in which an entirety of the clip mounted over the cap is proximal of the distal-most end of the endoscope.

In an embodiment, the distal end of the repositioning element may be connected to the cap, a remaining length of the cap extending distally between an interior surface of the cap and an exterior surface of an endoscope on which the cap is mounted and passed distally through a distal opening of a channel of the endoscope so that the repositioning element extends proximally through the channel of the endoscope to a proximal end.

In an embodiment, the repositioning element may be drawn proximally relative to the endoscope to move the cap distally relative to the endoscope, compressing the biasing element so that the cap and the clip mounted thereon are moved toward the review configuration.

In an embodiment, in the review configuration, gripping features may extend along the first and the second jaws to extend distally past the distal-most end of the endoscope so that the gripping features are in the field of view of the endoscope.

The present embodiments are also directed to a tissue clipping system, comprising a transparent cap configured to be mounted over a distal end of an endoscope, the cap extending longitudinally from a proximal end to a distal end and including a channel extending therethrough, the cap including a proximal portion configured to extend over the distal end of an endoscope on which the cap is mounted and a distal portion configured to extend distally past a distal end of an endoscope on which the cap is mounted. A clip is configured to be mounted over the cap, the clip including first and second jaws movably connected to one another via hinges, at least one of the hinges being biased to draw the first and second jaws toward one another. The clip is movable relative to the cap between an insertion configuration, in which the first and second jaws extend over opposing portions along the proximal portion of the cap so that the first and second jaws are separated from one another to receive target tissue therebetween, a review configuration, in which the clip is moved distally relative to the cap so that the clip extends over the distal portion of the cap to a position configured to be within a field of view of an optical system of an endoscope on which the cap is mounted, and a deployed configuration, in which the clip is moved distally off of the clip so that the first and second jaws are drawn toward one another under the bias of the at least one hinge. A deployment element is releasably coupled to the clip so that, when the deployment element is drawn proximally relative to the cap via a first distance, the clip is moved from the insertion configuration toward the review configuration, and when the deployment element is drawn further proximally relative to the cap a second distance, the clip is moved from the review configuration toward the deployed configuration. A repositioning element is releasably coupled to the clip so that, when it is desired to reposition the clip relative to a target tissue, the repositioning element is drawn proximally relative to the cap to move the clip from the review configuration toward the insertion configuration.

In an embodiment, a distal portion of the deployment element may be looped about the first jaw of the clip such that a portion of the distal portion of the deployment element is crimped between an interior surface of the cap and an exterior surface of an endoscope on which the cap is mounted and an enlargement at the distal end of the deployment element being is engaged between adjacent teeth of the first jaw, a remaining length of the deployment element extending proximally from the clip to be received within a distal opening of an endoscope on which the cap is mounted to extend proximally through a channel of the endoscope.

In an embodiment, when the clip is moved distally of the cap in the deployed configuration, the distal portion of the deployment element may become unwound from the first jaw such that the enlargement is disengaged from the clip and the clip is released from the deployment element to remain closed over the target tissue.

In an embodiment, the distal end of the repositioning element may releasably engage the second jaw of the clip, a remaining length of the repositioning element passing through a longitudinal slot extending through the cap.

In an embodiment, the cap may include a protrusion extending from an exterior surface of the cap, the protrusion configured to engage a portion of the clip when the clip is in the review configuration.

The present embodiments are also directed to a method for treating tissue. A clip is inserted to a target area in a body lumen via an endoscope, in an insertion configuration, in which the clip is mounted over a distal end of an endoscope via a transparent cap, a proximal end of the cap extending over the distal end of the endoscope and a distal portion of the cap extending distally of the distal end of the endoscope. The clip is mounted over the proximal portion of the cap so that jaws of the clip are separated from one another, in the insertion configuration. A suction force is applied through a working channel of the endoscope so that tissue is drawn into a channel of the cap and between the jaws of the clip. A deployment element releasably coupled to the clip is moved proximally relative to the endoscope so that the clip is moved toward a review configuration, in which the clip is moved distally along the cap to extend over the distal portion of the cap such that clip is in a field of view of the endoscope in the review configuration. When the clip is in the review configuration, it is determined whether the clip is in a desired position relative to a target tissue. The deployment element is moved further proximally relative to the endoscope to move the clip distally off of the cap toward a deployed configuration, in which the clip reverts toward a biased closed configuration in which the jaws are drawn toward one another to grip the tissue therebetween, when it is determined that the clip is in the desired position relative to the target tissue.

BRIEF DESCRIPTION

DETAILED DESCRIPTION

Figure 1:
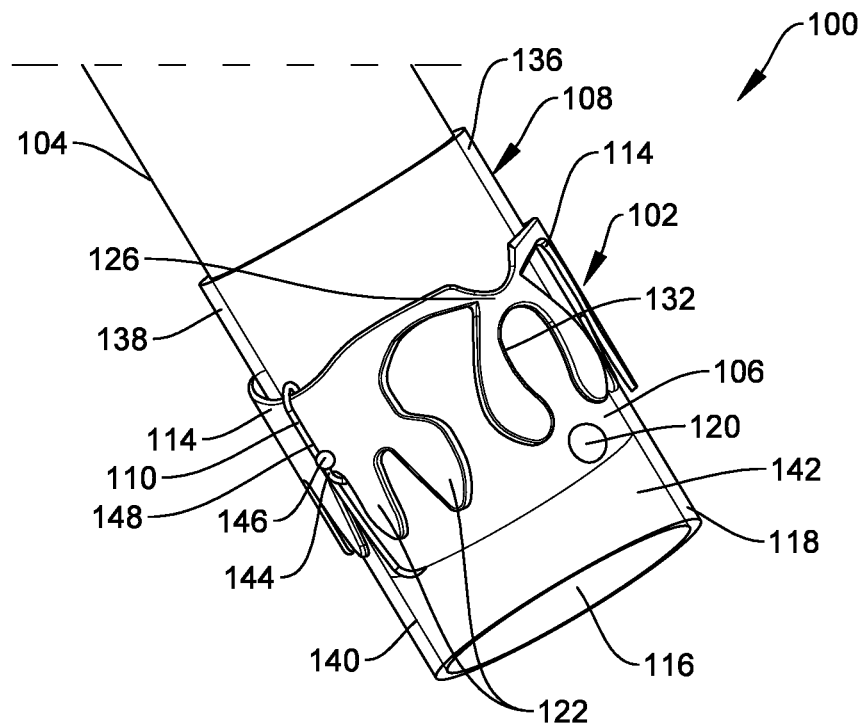
FIG. 1 shows a perspective view of a distal portion of a tissue clipping system according to an exemplary embodiment of the present disclosure, in an insertion configuration.
Figure 2:
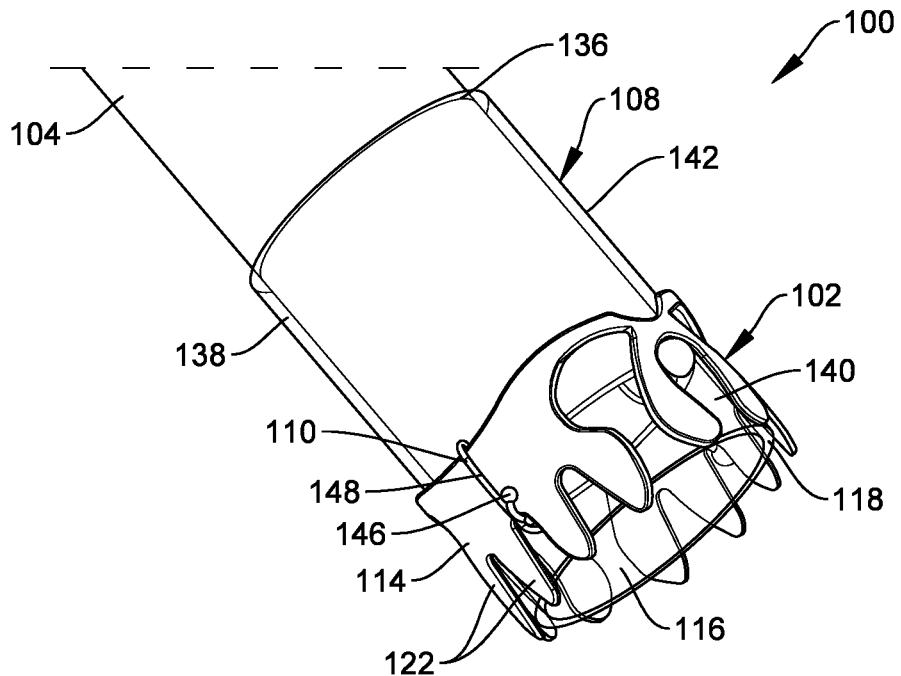
FIG. 2 shows another perspective view of the distal portion of the system of FIG. 1, in a review configuration.
Figure 3:
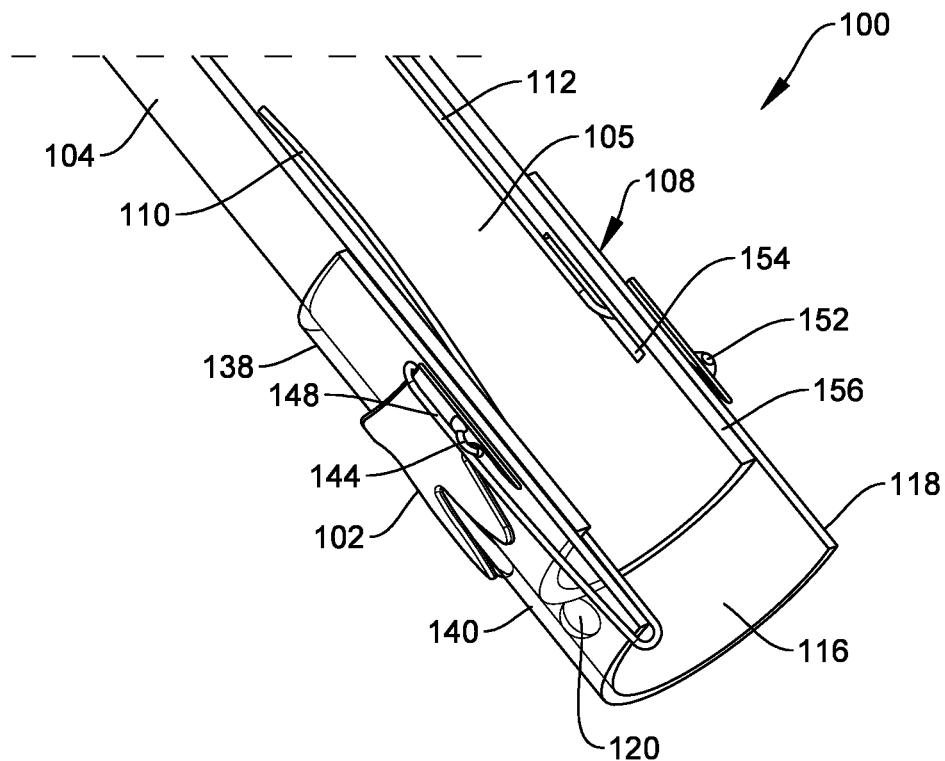
FIG. 3 shows a longitudinal cross-sectional perspective view of the distal portion of the system of FIG. 1.
Figure 4:
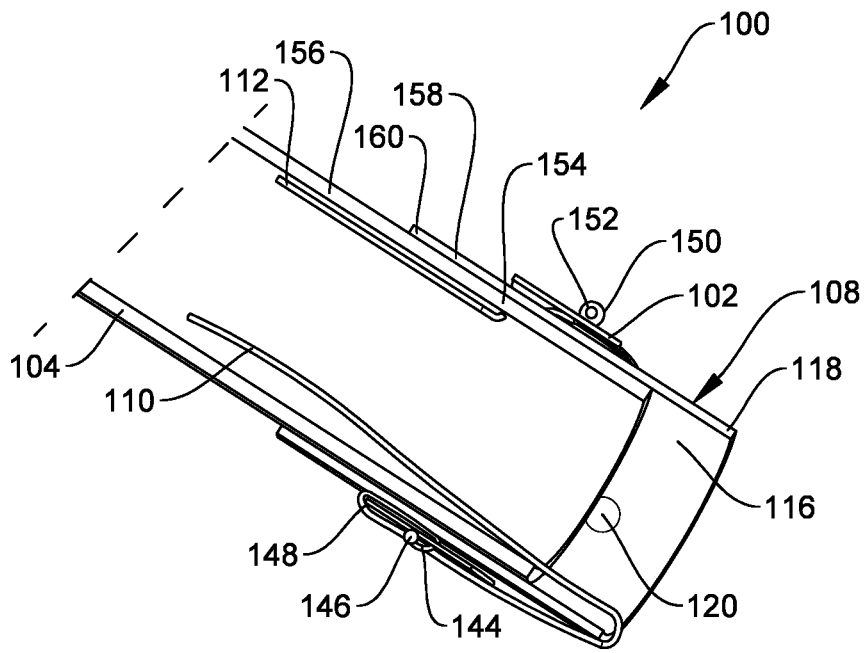
FIG. 4 shows another longitudinal cross-sectional side view of the distal portion of the system of FIG. 1.

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to a deployment thereof. Exemplary embodiments of the present disclosure comprise a clip mountable over a distal end of an endoscope via a cap. The clip is movable relative to the endoscope between an insertion configuration, a review configuration and a deployed configuration via one of a deployment element releasably coupled to the clip and a repositioning element coupled to one of the clip or the cap. The clip of the exemplary embodiments may be inserted to a target site within a body and positioned over a target tissue in the insertion configuration.

In the insertion configuration, the clip is mounted over the cap so that jaws of the clip are separated from one another toward an open configuration so that tissue may be received therebetween. In a review configuration, the clip is moved distally relative to the endoscope so that at least a portion of the clip extends within a field of view of the endoscope. In this review configuration, the clip remains mounted over the cap toward the open configuration, with the jaws separated from one another to receive target tissue therebetween, while also being visible via the endoscope so that an operator of the system may determine whether the clip is in a desired position relative to the target tissue. If the clip is determined to be in the desired position relative to the target tissue, the clip may be moved toward the deployed configuration via the deployment element. In the deployed configuration, the clip is moved distally off of the cap so that the clip reverts toward a biased closed configuration to grip the target tissue between the jaws thereof.

Once the clip has been deployed and is in the closed configuration, the clip is released from the endoscope to remain in the body, clipped over the target tissue. If, however, it is determined during the review configuration that the clip is not in a desired position relative to the target tissue, the clip may be drawn proximally relative to the endoscope via the repositioning element, back toward the insertion configuration so that the clip may be repositioned over the target tissue. This process may be repeated, as necessary, until it is determined that the clip is in the desired position relative to the target tissue. Upon determination that the clip is in the desired position relative to the target tissue, the clip is moved distally off of the clip toward the deployed configuration, in which the clip is clipped over the target tissue and completely separated from the endoscope so that the clip remains in the body over the target tissue.

It will be understood by those of skill in the art, that upon movement of the clip toward the deployed configuration, the clip is entirely separated from the endoscope and is permanently released within the body. It will be understood by those of skill in the art that terms proximal and distal, as used herein, are intended to refer to a direction toward and away from, respectively, a user of the device.

As shown in FIGS. 1-10, a clipping system 100 for treating tissue defects and/or perforations according to an exemplary embodiment of the present disclosure comprises a clip 102 configured to be mounted over a distal portion 106 of an endoscope 104 via a transparent cap 108. The clip 102 is releasably coupled to a deployment element 110, which is coupled to the clip 102 so that tensioning the deployment element 110 may move the clip 102 distally relative to the endoscope 104 (and the cap 108 mounted thereon) from an insertion configuration towards a review configuration and, upon determination via an operator of the system 100 (e.g., a surgeon) that the clip 102 is in a desired position relative to a target tissue, from the review configuration to a deployed configuration in which the clip 102 is released from the cap 108 and closed over target tissue.

The clip 102 is also releasably coupled to a repositioning element 112 so that if, upon viewing the clip 102 in the review configuration, it is determined that the clip 102 is not in the desired position relative to the target tissue, the repositioning element 112 may be tensioned to draw the clip 102 proximally relative to the cap 108 from the review configuration back toward the insertion configuration so that the clip 102 may be repositioned relative to the target tissue. In the insertion configuration, the clip 102 is mounted over the cap 108 so that the cap 108 holds the clip 102 in an open position with jaws 114 of the clip 102 spread apart from one another about the cap 108 so that tissue to be clipped may be drawn through a channel 116 of the cap 108 and between the jaws 114. In this insertion configuration, an entirety of the clip 102 (including the jaws 114) is proximal a distal end 118 of the cap 108 minimizing any obstruction of the visual field of the optical system of the endoscope 104 so that the user may fully observe the tissue adjacent to the cap 108.

To move the clip 102 from the insertion configuration toward the review configuration, the deployment element 110 is tensioned to push the clip 102 distally along the cap 108 until a portion of the clip 102 abuts against a protrusion 120 formed on the cap 102. This provides tactile feedback to the operator indicating that the clip 102 is in the review configuration. In the review configuration, the jaws 114 remain mounted over a distal portion 140 of the cap 108, which extends distally past the distal end 106 of the endoscope 104, with the jaws 114 maintained open and separated from one another. In one embodiment in the review configuration, tips of teeth 122 of the jaws 114 extend distally past the distal end 118 of the cap 108 and the clip 102 while the clip 102 remains mounted over the cap 108 with the jaws 114 open. Since the cap 108 is transparent, when the clip 102 is mounted over the distal portion 140 of the cap 108, the clip 102 is within a field of view of an optical system of the endoscope 104.

In the review configuration, the operator may visually determine whether the clip 102 is in the desired position relative to the target tissue. If, the clip 102 is in the desired positioned, the target tissue is drawn into the cap 108 (e.g., by applying suction through a working channel of the endoscope 104). The clip 102 is then deployed by tensioning the deployment element 110 until a force exerted thereon exceeds a predetermined force which pushes the clip 102 over the protrusion 120, off of the cap 108. When the clip 102 is pushed off the cap 108, the jaws 114 of the clip 102 close under their natural bias gripping the tissue that had been drawn into the cap 108.

Figure 5:
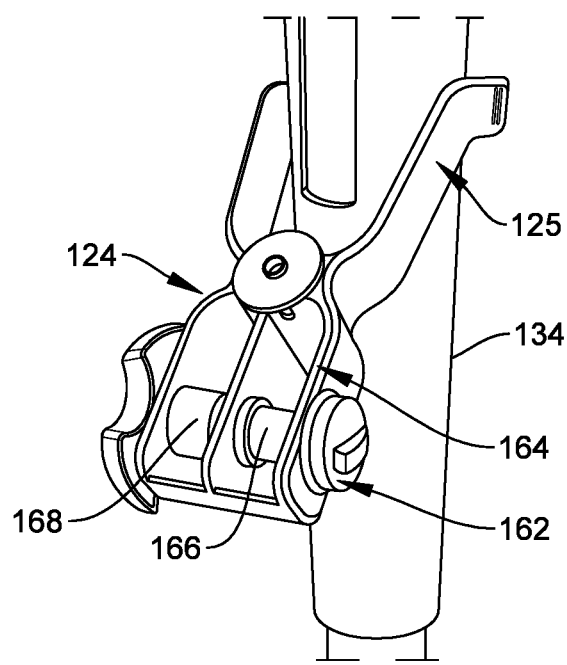
FIG. 5 shows a perspective view of an actuator assembly according to the exemplary system of FIG. 1.

If, however, the operator determines during the review configuration that the clip 102 is not in a desired position relative to the target tissue, tension is applied to the repositioning element 112 to draw the clip 102 proximally relative to the endoscope and the endoscopic cap 108, from the review configuration toward the insertion configuration. The clip 102 may be moved between the insertion configuration and the review configuration so that the device may be repositioned until it is determined that the clip 102 is in the desired position relative to the target tissue. Once it has been determined that the clip 102 in the desired position relative to the target tissue, the clip 102 is deployed, as described above. As will be described in further detail below, the deployment element 110 and the repositioning element 112 may be used to move the clip 102 between the insertion, review, and deployed configurations. As will also be described in further detail below, movement of the deployment and repositioning elements 110, 112 may be controlled via an actuating assembly 124 attached to a proximal end of the endoscope 104, as shown in FIG. 5.

The clip 102 may be mounted to any standard endoscope 104 via the cap 108 which is sized, shaped and configured to be mounted over the distal end 106 of the endoscope 104 (e.g., slid over the distal end 106 and retained thereon via a friction fit). As will be understood by those of skill in the art, the endoscope 104 is configured to be inserted through a body lumen to a target area within the lumen and thus, must be sufficiently flexible to navigate through even tortuous paths of the body lumen. According to an exemplary embodiment, a distal portion of the endoscope 104 includes a longitudinal slot 154 extending through a wall 156 thereof. The longitudinal slot 154 is sized and configured to receive the repositioning element 112 therein, as will be described n further detail below.

A proximal end of the endoscope 104 may include a handle member 134 via which a physician or other user may guide the endoscope through the body lumen (e.g., gastrointestinal tract) to a target site. The actuating assembly 124, which will be described in further detail below, may be coupled to the handle member 134 of the endoscope 104. In an alternative embodiment, the cap 108 may be sized and shaped to be mounted over the distal end of any insertion device (flexible or rigid) suitable for accessing a target site within a body at which a tissue to be clipped is located.

The cap 108 extends longitudinally from a proximal end 136 to the distal end 118 and includes the channel 116 extending longitudinally therethrough. The cap 108 is configured to be mounted over the distal end 106 of the endoscope 104 so that the channel 116 of the cap 108 is substantially aligned with a longitudinal axis of the endoscope 104 and in communication with a channel 105 of the endoscope 104. The channel 116 extends away from the distal end 106 of the endoscope 104 so that occlusion of the field of view of the endoscope is minimized. The cap 108 is sized and shaped to correspond to a cross-sectional shape of the endoscope 104 so that the cap 108 fits thereover via a friction fit. The cap 108 is configured so that, when the cap 108 is mounted over the distal end 106 of the endoscope, a proximal portion 138 of the cap 108 extends over the endoscopic shaft 106 while the distal portion 140 of the cap 108 extends distally past the distal end 106 of the endoscope 104. The cap 108 is formed of a transparent material so that portions of the clip 102 extending over the distal portion 140 of the cap 108, or there beyond, are within the field of view of the endoscope 104. According to one exemplary embodiment, a length of the distal portion 140 of the cap 108 may be selected so portions of the clip 102 remain visible even when tissue is suctioned into the cap 108. In one example, there may be a gap of approximately 10 mm between a proximal end of an area of visibility and the tissue that has been suctioned into the cap 108 so that a position of the clip 102 relative to the suctioned tissue remains visible to the user when tissue is suctioned into the cap 108.

The cap 108 includes the protrusion 120 extending from an exterior surface 142 thereof and configured to engage a portion of the clip 102. In one embodiment, the cap 108 includes a pair of protrusions 120 diametrically opposed from one another and positioned along the cap 108 so that, when the clip 102 engages the protrusion 120, the clip 102 extends over the cap 108 in the review configuration. The protrusion 120 is sized, shaped and configured so that, when a distal force exceeding a predetermined threshold value is applied to the clip 102, the clip 102 is moved distally over the protrusion toward the deployed configuration.

The proximal portion 138 of the cap 108 may include a longitudinal slot 158 extending through a wall 160 thereof. The longitudinal slot 158 may substantially correspond in size and shape to the longitudinal slot 154 of the endoscope 104 so that, when the cap 108 is mounted over the distal end 106 of the endoscope 104, the longitudinal slot 158 of the cap 108 is substantially aligned with the longitudinal slot 154 of the endoscope 104. As will be described in further detail below, the repositioning element 112 may pass through the longitudinal slots 154, 158 so that a portion of the repositioning element 112 extends through the endoscope 104 to the actuating assembly 124.

The clip 102 includes a pair of jaws 114 connected to one another via hinges 126, which permit movement of the jaws 114 relative to one another between the open configuration, in which the jaws 114 are separated from one another, and the closed configuration, in which the jaws 114 are moved toward one another. Each of the jaws 114 may extend along a curve from a first end 128 to a second end 130 so that a first one of the hinges 126 connects the first ends 128 of each of the jaws 114, while a second one of the hinges 126 connects the second ends 130 of each of the jaws 114. According to one exemplary embodiment, the hinges 126 may be a living hinge including a groove 132 sized and shaped to engage the protrusion 120 of the cap 108 therein. The hinges 126 may be spring biased, biasing the jaws 114 toward the closed configuration. In one exemplary embodiment, each of the jaws 114 include gripping features such as, for example, teeth 122, so that when the jaws 114 are moved toward one another toward the closed configuration, tissue may be gripped between the jaws 114 via the teeth 122.

When the clip 102 is mounted over the cap 108, the jaws 114 extend over opposing portions of the cap 108 so that the exterior surface 142 of the cap 108 holds the clip 102 open with the jaws 114 separated from one another in the open configuration. In the open configuration, tissue may be drawn into the channel 116 of the cap 108 and between the jaws 114 via, for example, a suction force applied through the endoscope 104 or a grasping device inserted through a working channel of the endoscope 104. In the insertion configuration, the clip 102 may be mounted over the proximal portion 138 of the cap 108.

In the review configuration, however, the clip 102 is moved distally relative to the cap 108 until the grooves 132 of the clip 102 engage the protrusions 120 and the clip 102 extends over the distal portion 140 of the cap 108. In one embodiment, the teeth 122 of the clip 102 extend distally past the distal end 118 of the cap 108. Thus, the clip 102, and the position of the teeth 122 relative to the target tissue, is visible to the operator via the optical system of the endoscope 104. When the clip 102 is moved distally off the cap 108, however, the clip 102 is permitted to revert to its biased closed configuration to grip the received between the jaws 114. It will be understood by those of skill in the art that the hinges 126 and/or jaws 114 of the clips 102 may be formed of any of a variety of materials so long as the hinges 126 bias the jaws 114 toward the closed configuration, as described above. In one example, portions of the clip 102 (e.g., the hinges 126) may be formed of a shape memory alloy such as, for example, Nitinol.

As described above, the clip 102 may be moved relative to the cap 108 from the insertion configuration toward the review configuration and from the review configuration toward the deployed configuration via the deployment element 110. The deployment element 110 may be formed as a thread, wire, strand, filament or other similar flexible longitudinal element extending from a distal end 144 releasably coupled to the clip 102 to a proximal end connected to the actuating assembly 124.

According to an exemplary embodiment, the distal end 144 includes an enlarged end which, in one example, may be configured as a knot 146. A distal portion 148 of the deployment element 110 is looped about a portion of the clip 102 so that a portion of the deployment element 110 is crimped between the clip 102 and the exterior surface 142 of the cap 108 so that the knot 146 engages a portion of the clip 102. A remaining length of the deployment element 110 extends distally from the clip 102 so that it may extend through a distal opening of the channel 116 of the cap 108, proximally through the channel 116 and the working channel of the endoscope 104 to the actuating assembly 112. In one embodiment, the distal portion 148 of the deployment element 110 may be looped about a first one of the jaws 114 so that the knot 146 engages the clip 102 between two adjacent teeth 122.

More specifically, the knot 146 at the distal end 144 of the deployment element 110 is engaged between the adjacent teeth 122, looped about the first one of the jaws 114 so that a portion of the deployment element 110 immediately proximal of the knot 146 is crimped between the clip 102 and the exterior surface 142 of the cap 108, the distal portion 148 being looped about the first jaw 114 so that the remaining length of the deployment element 110 extends distally from the clip 102, through the distal opening of the channel 116 of the cap, and proximally through the channel 116 and the working channel of the endoscope 104. Thus, when the deployment element 110 is drawn proximally relative to the endoscope 104, applying a tension thereto, the clip 102 is moved distally relative to the cap 108.

When the clip 102 is mounted over the cap 108 in the insertion configuration, the deployment element 110 may be drawn proximally relative to the endoscope 104 via a first distance selected so that the grooves 132 of the clip 102 abut the protrusions 120 and the clip 102 is in the review configuration. From the review configuration the deployment element 110 may be drawn further proximally relative to the endoscope 104 via a second distance, applying a force exceeding the predetermined threshold value, so that the clip 102 is moved distally over the protrusion 120 toward the deployed configuration. When the clip 102 is moved distally off of the cap 108 toward the deployed configuration, the distal portion 148 of the deployment element 110 will unravel, disengaging the clip 102 and thereby releasing the clip 102 within a body, over the target tissue. Thus, it will be understood by those of skill in the art that the deployment element 110 must be able to withstand forces exceeding the predetermined threshold value.

As described above, when it is determined that the clip 102 is not in a desired position relative to the target tissue, the clip 102 may be drawn proximally relative to the cap 108 to move the clip 102 from the review configuration toward the insertion configuration via the repositioning element 112. Similarly to the deployment element 110, the repositioning element 112 may be formed as a thread, wire, strand, filament or other similar flexible longitudinal element extending from a distal end 150 releasably coupled to the clip 102 to a proximal end connected to the actuating assembly 124.

According to one exemplary embodiment, the repositioning element 112 may engage the second one of the jaws 114 so that the repositioning element 112 extends along a portion of the endoscope 104 substantially opposing the deployment element 110. Similarly to the deployment element 110, the distal end 150 of the repositioning element 112 includes an enlarged end configured as, for example, a knot 152. In one embodiment, the knot 152 may engage the clip 102 between adjacent teeth 122 of the second jaw 114. A portion of the repositioning element 112 immediately proximal of the knot 152 is crimped between the clip 102 and the exterior surface 142 of the cap 108 so that a remaining length of the repositioning element 112 passes through the longitudinal slot 158 of the cap 108 and the longitudinal slot 154 of the endoscope 104 to extend through the channel 105 of the endoscope 104. Thus, when the repositioning element 112 is moved proximally relative to the endoscope 104, the clip 102 may be moved proximally relative to the cap 108 from the review configuration toward the insertion configuration.

It will be understood by those of skill in the art that a length and a position of the longitudinal slots 154, 158 along the endoscope 104 and cap 108, respectively, is selected so that the clip 102 cannot be moved proximally beyond the cap 108. When the clip 102 is moved distally off the cap 108 toward the deployed configuration (via the deployment element 110), the repositioning element 112 is released from between the clip 102 and the exterior surface 142 of the cap 108 and the knot 152 disengages the clip 102 to release the clip in the body over the target tissue.

The actuating assembly 124 may be used to actuate the deployment element 110 and the repositioning element 112. As described above, the actuating assembly 124 may be coupled to the handle member 134 at the proximal end of the endoscope 104 and connected to the proximal ends of the deployment element 110 and the repositioning element 112. The actuating assembly 124 may be coupled to the handle member 134 via any of a number of coupling elements 125 including, for example, a snap interface.

In one embodiment, the actuating assembly 124 includes two actuating elements—e.g., a first knob 162 for controlling the deployment element 110 and a second knob 164 for controlling the repositioning element 112. The first and second knobs 162, 164 may be configured, for example, as thumb wheels so that the user of the system 100 may easily control a movement of the deployment element 110 and repositioning element 112 as they are holding the endoscope 104 via the handle member 134. As will be understood by those of skill in the art, a proximal end of the deployment element 110 may extend proximally from the channel 105 of the endoscope 104 to be wound around a first rotary wheel 166 that is connected to the first knob 162 so that a rotation of the first knob 162 correspondingly rotates the first rotary wheel 166, thereby moving the deployment element 110 as desired. For example, a rotation of the first knob 162 moves the deployment element proximally relative to the endoscope 104 and the cap 108, applying a tension to the deployment element 110 which moves the clip 102 relative to the cap 108 from the insertion configuration toward the review configuration, or from the review configuration toward the deployed configuration.

Similarly, the second knob 164 may be connected to a second rotary wheel 168 about which a proximal end of the repositioning element 112 may be wound so that a rotation of the second knob 164 controls a movement of the repositioning element 112, and thereby the clip 102. For example, a rotation of the second knob 164 moves the repositioning element 112 proximally relative to the endoscope 104 and the cap 108 so that the clip 102 is correspondingly moved proximally relative to the cap 108 from the review configuration toward the insertion configuration.

Figure 6:
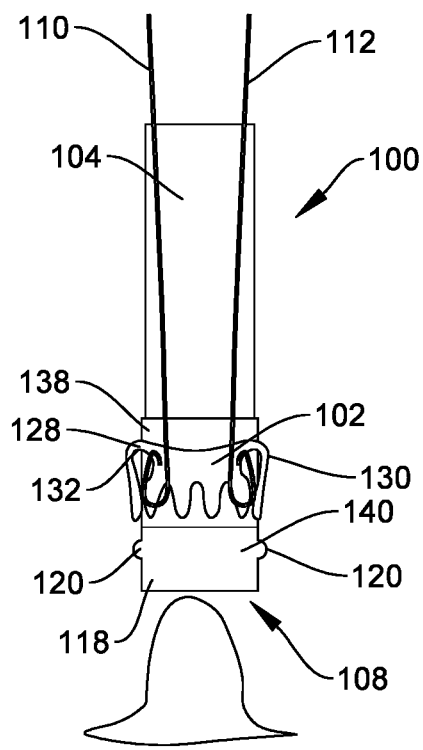
FIG. 6 shows a longitudinal side view of the system of FIG. 1, in the insertion configuration.

According to an exemplary method for tissue closure utilizing the clipping system 100, as shown in FIGS. 6-10, the clip 102 may be inserted through a body lumen such as, for example, the gastrointestinal tract, to a target area within the body lumen via the endoscope 104. As described above, in the insertion configuration, as shown in FIG. 6, the clip 102 is mounted over the proximal portion 138 of the cap 108, which is mounted over the distal end 106 of the endoscope 104, so that jaws 114 are separated from one another toward the open configuration. The clip 102 is guided to the target area via the endoscope 104 and positioned over a target tissue. A suction force may be applied through a working channel of the endoscope 104 so that the target tissue may be drawn into the channel 116 of the cap 108.

Figure 7:
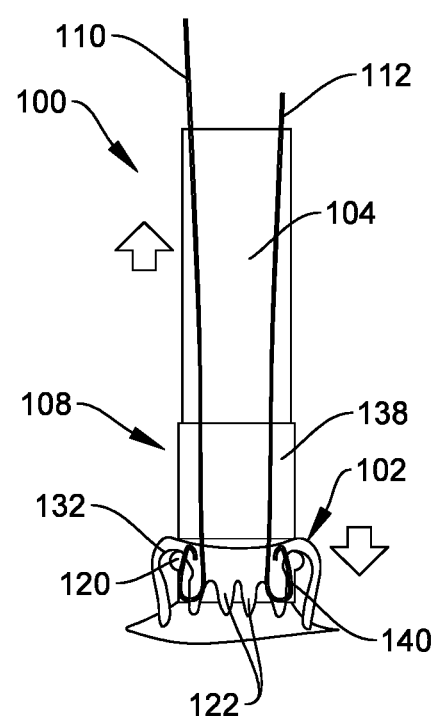
FIG. 7 shows a longitudinal side view of the system of FIG. 1, in the review configuration.

As shown in FIG. 7, the clip 102 may then be moved toward the review configuration by moving the clip 102 distally relative to the cap 108 via the deployment element 110. In particular, the deployment element 110 may be moved proximally relative to the endoscope 104 until the groove 132 of the clip 102 engages the protrusion 120 of the cap 108, providing tactile feedback to the user which indicates that the clip 102 is in the review configuration. In the review configuration, the clip 102 extends over the distal portion 140 of the cap 108 and teeth 122 may extend distally past the distal end 118 thereof so that a position of the clip 102 relative to the target tissue is within the field of view of the endoscope 104. Thus, in the review configuration, the user may determine whether the clip 102 is in the desired gripping position relative to the target tissue.

Figure 10:
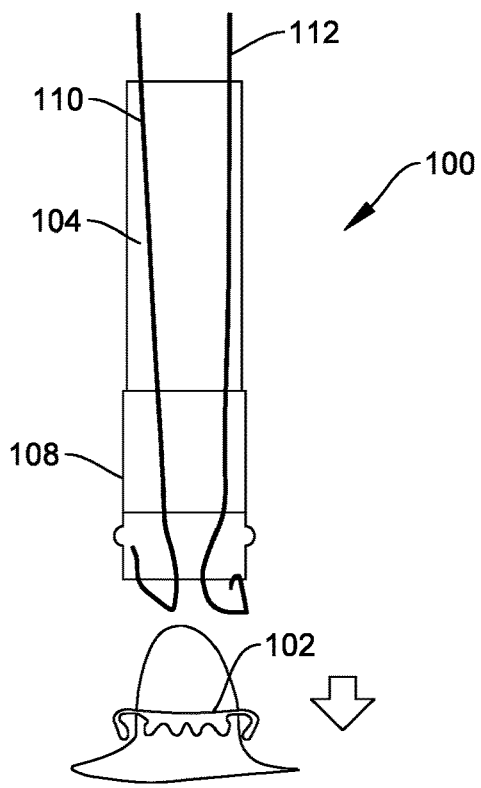
FIG. 10 shows a longitudinal side view of the system of FIG. 1, in a deployed configuration.
Figure 11:
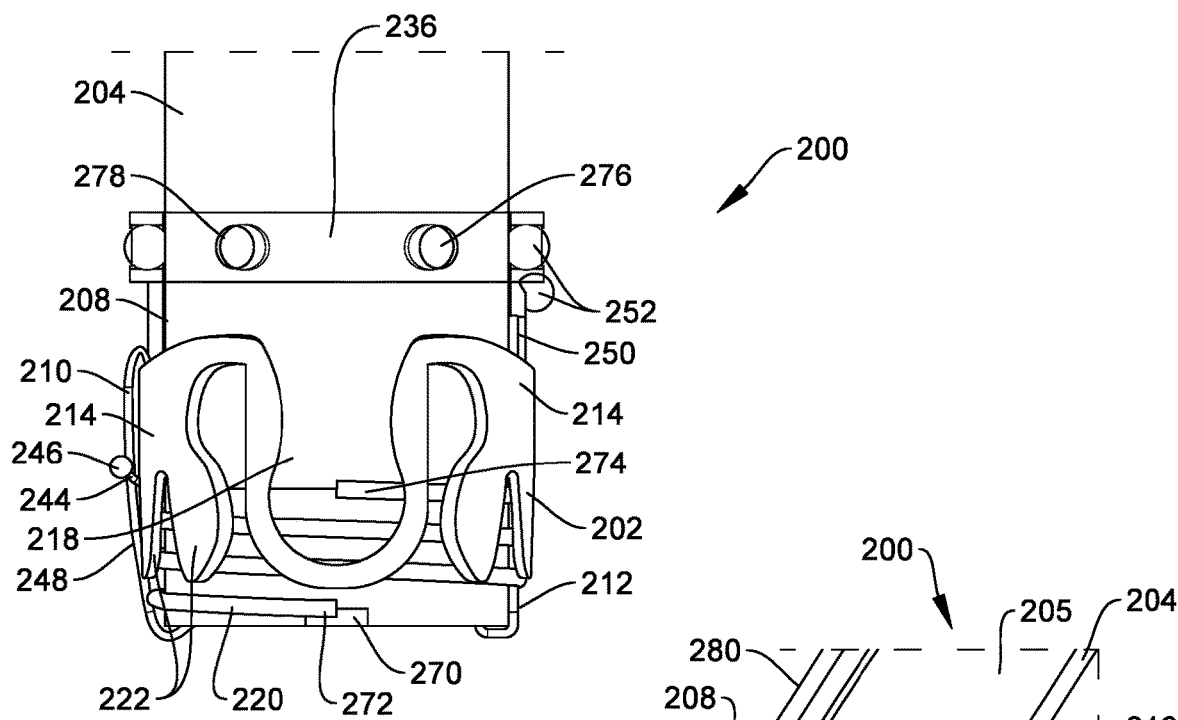
FIG. 11 shows a longitudinal side view of a distal portion of a tissue clipping system according to another exemplary embodiment of the present disclosure.
Figure 12:
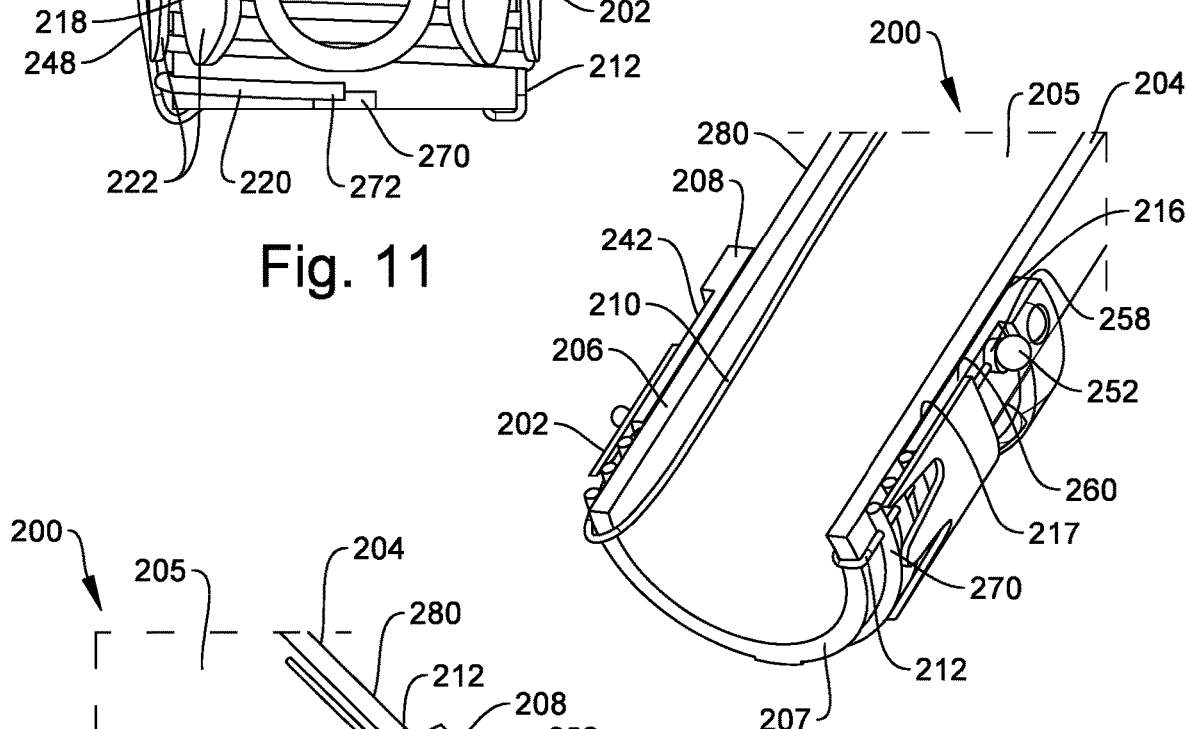
FIG. 12 shows a longitudinal cross-sectional perspective view of the distal portion of the system of FIG. 11.
Figure 13:
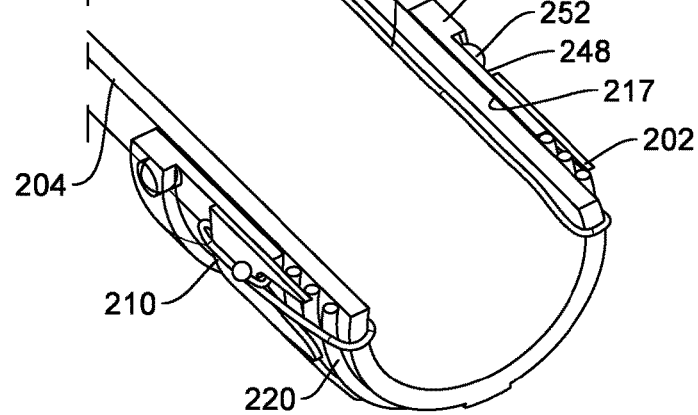
FIG. 13 shows another longitudinal cross-sectional perspective view of the distal portion of the system of FIG. 11.

If it is determined that the clip 102 is in the desired position relative to the target tissue, the deployment element 110 may be moved further proximally relative to the endoscope 104 so that a force exerted on the deployment element 110 exceeds a predetermined threshold level, which allows the clip 102 to be moved distally over the protrusion 120 of the cap 108 toward the deployed configuration (see FIG. 10). The clip 102 is moved distally relative to the cap 108 until the clip is moved distally off the cap 108 and the clip 102 is permitted to revert to its biased closed configuration, thereby gripping the target tissue therebetween. As described above, when the clip 102 is moved toward the deployed configuration, each of the deployment element 110 and the repositioning element 112 disengage the clip 102 releasing the clip 102 in the body, clipped over the target tissue.

Figure 8:
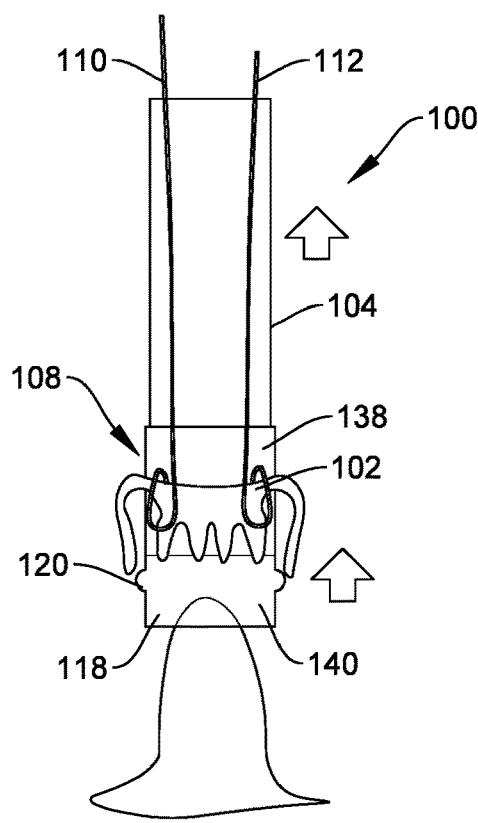
FIG. 8 shows a longitudinal side view of the system of FIG. 1, moving toward the insertion configuration.
Figure 9:
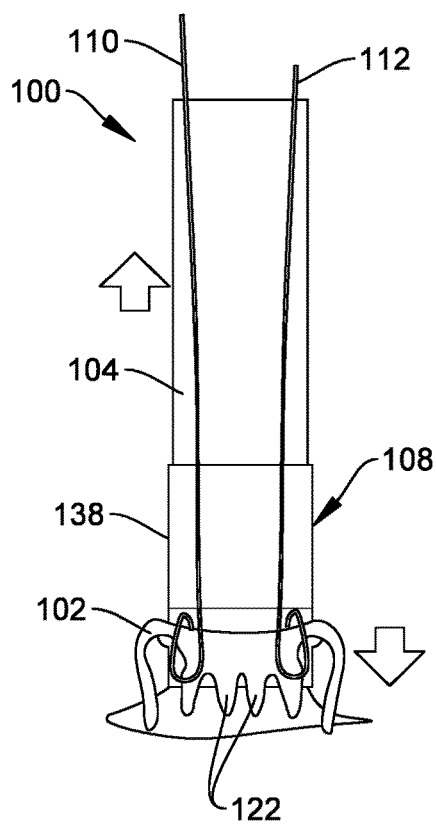
FIG. 9 shows a longitudinal side view of the system of FIG. 1, moving toward the review configuration.

If, however, it is determined during the review configuration that the clip 102 is not in the desired position relative to the target tissue, the clip 102 may be moved from the review configuration proximally along the cap 108 toward the insertion configuration, as shown in FIG. 8. As described above, the repositioning element 112 may be drawn proximally relative to the endoscope 104, thereby moving the clip 102 proximally relative to the cap 108 until the clip 102 extends over the proximal portion 138 of the cap 108. The clip 102 may then be repositioned over the target tissue, as desired, and the clip 102 once again moved toward the review configuration, as shown in FIG. 9. This process may be repeated, as necessary, until the user is able to visually confirm that the clip 102 has been clipped over the target tissue, as desired. Once the user confirms that the target tissue has been clipped, as desired, the clip 102 may be moved from the review configuration to the deployed configuration, as described above and as shown in FIG. 10, to release the clip 102 from the endoscope 104.

As shown in FIGS. 11-21, a tissue clipping system 200 according to another exemplary embodiment may be substantially similar to the tissue clipping system 100, comprising a clip 202 mountable over a distal end 206 of an endoscope 204 via a cap 208 so that the clip 202 is movable relative to the endoscope 204 between an insertion configuration, a review configuration and a deployed configuration via one of a deployment element 210 and a repositioning element 212 releasably coupled to the clip 202. Similarly to the system 100, in the insertion configuration the clip 202 is mounted over the cap 208 in an open position in which jaws 214 thereof are separated from one another to receive tissue therebetween. The clip 202 may be inserted to a target site within a body in this insertion configuration. In a review configuration, the clip 202 is moved distally relative to the endoscope 204 to enhance a field of view of the endoscope 204 so that a position of the clip 202 relative to the target tissue is visible to an operator (e.g., surgeon or other user) of the system 200.

Rather than moving the clip 202 relative to the cap 208, however, the cap 208—with the clip 202 mounted thereon—is moved distally relative to the endoscope 204 to move the clip 202 from the insertion configuration toward the review configuration. The clip 202 is mounted over the cap 208 such that a portion of the clip 202 extends distally past a distal end 218 of the cap 208 while maintaining the clip 202 in the open position so that, when the cap 208 is moved distally relative to the endoscope 204 toward the review configuration, a portion of the clip 202 extends distally of the distal end 206 of the endoscope 204 so that the portion of the clip 202 extending distally beyond the distal end 206 is within the field of view of the endoscope 204.

In one example, there may be a gap of approximately 10 mm between a proximal end of an area of visibility and the tissue that has been suctioned into the cap 108 so that a position of the clip 202 relative to the suctioned tissue remains visible to the user even when tissue is suctioned into the cap 108. If the operator determines that the clip 202 is in a desired position relative to the target tissue, the clip 202 may be moved from the review configuration toward the deployed configuration. If, however, the operator determines that the clip 202 is not in the desired position relative to the target tissue, the clip 202 may be moved from the review configuration back toward the insertion configuration so that the clip 202 may be repositioned relative to the target tissue.

To facilitate movement of the cap 208 and clip 202 relative to the endoscope 204 between the insertion configuration and the review configuration, the system 200 further comprises a biasing element 220 extending from a proximal end 274 to a distal end 272 between the cap 208 and a distal-most end 207 of the endoscope 204 to bias the cap 208, and the clip 202 mounted thereover, toward the insertion configuration. The repositioning element 212, a distal end 250 of which is connected to the cap 208, may be used to move the cap 208 and clip 202 between the insertion configuration and the review configuration, as necessary, until the operator determines that the clip 202 is in the desired configuration relative to the target tissue. Once the operator has determined that the clip 202 is in the desired position relative to the target tissue, the deployment element 210, a distal end 244 of which is releasably coupled to the clip 202, may be used to move the clip 202 distally off of the cap 208 toward the deployed configuration. In the deployed configuration, the clip 202 reverts toward a biased closed configuration to grip the target tissue between jaws 214 thereof. Manipulation of the deployment element 210 and/or the repositioning element 212 for moving the clip 202 between the insertion, review and deployed configurations may be controlled via an actuator assembly 224 at a proximal end of the endoscope 204.

The endoscope 204 may be substantially similar to the endoscope 104. The endoscope 204 may extend longitudinally from a proximal end including a handle member 234 to the distal end 206, over which the cap 208 is mounted, and includes a channel 205 extending therethrough. In this embodiment, the endoscope 204 further includes a stop 270, shoulder or other protrusion extending from an exterior surface 242 of the cap 208, at the distal-most end 207, for engaging the distal end 272 of the biasing element 220 and stopping the distal end 272 of the biasing element 220 from extending distally beyond the stop 270.

The cap 208 may also be substantially similar to the cap 108, extending longitudinally from a proximal end 236 to a distal end 218 and including a channel 216 therein. The channel 216 corresponds to a size of the endoscope 204 so that the cap 208 may be movably mounted thereover. In one exemplary embodiment, to facilitate a movement of the cap 208 relative to the endoscope 204, the cap 208 may include a plurality of roller balls 276 received within correspondingly shaped recesses 278 of the cap 208 so that the roller balls 276 are rotatable within the recesses 278 and movable along the exterior surface 242 of the cap 208. The cap 208 also includes an opening 258 extending through a wall 260 thereof, the opening 258 configured to receive the repositioning element 212 therein, as will be described in further detail below.

The biasing element 220 may extend between the distal end 218 of the cap 208 and the stop 270 of the endoscope 204 to bias the cap 208 toward the insertion configuration. According to one exemplary embodiment, the biasing element 220 may be configured as a spring extending about the distal end 206 of the endoscope 204, between the distal end 218 of the cap 208 and the stop 270 at the distal-most end 207 of the endoscope 204. In the insertion configuration, the clip 202, which is substantially similar to the clip 102, is mounted over the cap 208 so that jaws 214 of the clip 202 extend over opposing portions of the cap 208. The exterior surface 242 of the cap 208 holds the jaws 214 open so that the jaws 214 are separated from one another and tissue may be received therebetween. The clip 202 may be mounted over the cap 208 so that, for example, teeth 222 extend distally past the distal end 218 of the cap 208. In the insertion configuration, however, the distal end 218 of the cap 208 is separated from the distal-most end 207 of the endoscope 204 via a distance selected so that the teeth 222 do not extend distally past the distal-most end 207 of the endoscope 204.

To move the clip 202 toward the review configuration, the cap 208 is moved distally relative to the endoscope 204, compressing the biasing element 220 until the teeth 222 extend distally past the distal-most end 207 of the endoscope 206 so that the teeth 222 is within the field of view of the endoscope 204. Thus, in the review configuration, the operator or user may determine whether the clip 202 is in the desired position relative to the target tissue. If the clip 202 is in the desired position, the clip 202 may be moved toward the deployed configuration by pushing the clip 202 distally off of the cap 208. If, however, it is determined that the clip 202 is not in the desired position relative to the target tissue, the compression force on the biasing element 220 is released so that the biasing element 220 reverts to its biased configuration, pushing the cap 208 proximally along the endoscope 204 toward the insertion configuration so that the clip 202 may be repositioned, as necessary. As will be described in further detail below, movement of the clip 202 between the insertion configuration and the review configuration is controlled via the repositioning element 212 and movement of the clip 202 from the review configuration toward the deployed configuration is controlled via the deployment element 210.

The deployment element 210 may be substantially similar to the deployment element 110 and may include, for example, a thread, wire, strand, filament or other similar flexible longitudinal element extending from the distal end 244 releasably coupled to the clip 202 to a proximal end connected to the actuator assembly 224. The deployment element 210 may be releasably coupled to the clip 202 in a manner substantially to the deployment element 110.

In an exemplary embodiment, a distal portion 248 of the deployment element 210 may be looped about a portion of a first one of the jaws 214 so that a portion of the deployment element 210 is crimped between the clip 202 and the exterior surface 242 of the cap 208 while, for example, a knot 246, at the distal end 244 may be engaged between adjacent teeth 222 of a first one of the jaws 214. A remaining length of the deployment element 210 extends distally from the clip 202 to be received within a distal opening of the channel 205 and to extend proximally therethrough. Thus, drawing the deployment element 210 proximally relative to the endoscope 204 moves the clip 202 distally relative to the cap 208 so that the clip 202 may be moved toward the deployed configuration. As described above, when the clip 202 is pushed distally off of the cap 208 toward the deployed configuration, the distal portion 248 of the deployment element 210 becomes unwound from the clip 202 so that the knot 246 disengages the clip 202 and the clip 202 is released within the body over the target tissue.

The repositioning element 212 may be substantially similar to the repositioning element 112 including, for example, a thread, strand, wire filament or other similar flexible longitudinal element. Rather than being releasably connected to the clip 202, however, the distal end 250 of the repositioning element 212 may be non-releasably affixed to a portion of the cap 208. According to one exemplary embodiment, the distal end 250 includes an enlarged end such as, for example, a knot 252, so that when the repositioning element 212 is passed through the opening 258 extending through the wall 260 of the cap 208, the knot 252 prevents the distal end 250 from passing therethrough. Thus, the knot 252 of the repositioning element 212 engages the cap 208 along the exterior surface 242 of the cap 208 so that a remaining length of the repositioning element 212 extends through the opening 258, distally between an interior surface 217 of the cap 208 and an exterior surface 280 of the endoscope 204, distally between the biasing element 220 and the exterior surface 280 so that the repositioning element 212 is received within the distal opening of the channel 205 to extend proximally therethrough. Thus, the repositioning element 212 may be moved proximally relative to the endoscope 204 to move the cap 208 distally relative to the endoscope 204 from the insertion configuration toward the review configuration. In this review configuration the biasing element 220 is maintained in a compressed configuration via a tension maintained along the repositioning element 212. If, however, it is determined during the review configuration that the clip 202 is not in the desired position relative to the target tissue, the tension along the repositioning element 212 may be released to permit the biasing element 220 to revert to its biased configuration, thereby moving the cap 208 proximally relative to the endoscope 204, from the review configuration toward the insertion configuration.

Figure 14:
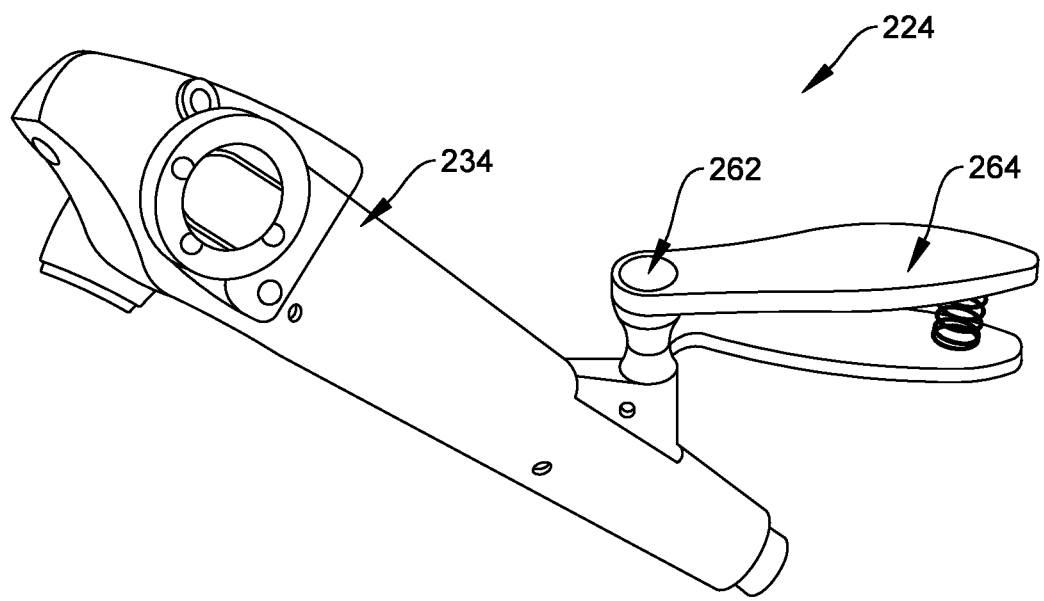
FIG. 14 shows a perspective view of an actuator assembly according to the exemplary system of FIG. 11.
Figure 15:
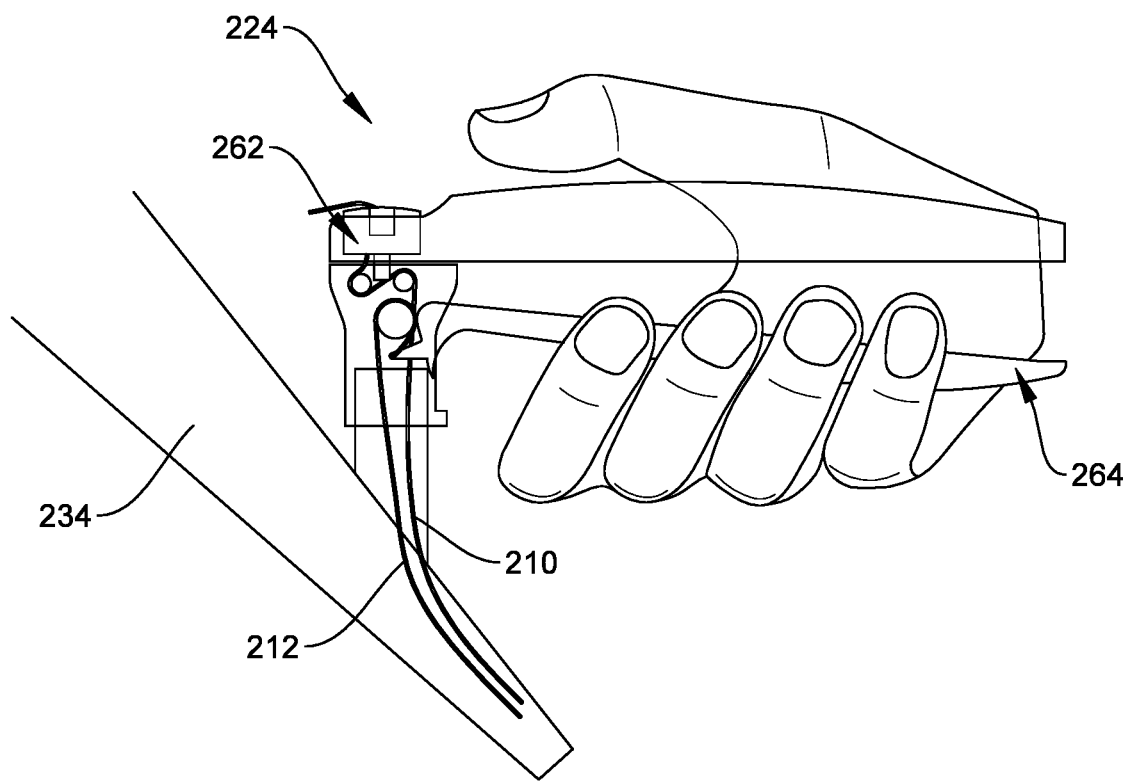
FIG. 15 shows a cross-sectional view of the actuator assembly of FIG. 14.

Proximal ends of each of the deployment element 210 and the repositioning element 212 may be connected to the actuator assembly 224 which, in one exemplary embodiment, may be coupled to the handle member 234 of the endoscope 204, as shown in FIGS. 14-15. According to an exemplary embodiment, the actuator assembly 224 may include a lever 264 configured to control a movement of the repositioning element 212 relative to the endoscope 204 and a push button 262 for controlling a movement of the deployment element 210 relative to the endoscope 204. For example, the proximal end of the repositioning element 212 is connected to the lever 264 such that, when the lever 264, is pressed, the repositioning element 212 is moved proximally relative to the endoscope 204, thereby moving the cap 208 distally relative to the endoscope from the insertion configuration toward the review configuration. The lever 264 should remain pressed to maintain the tension along the repositioning element 212 and keep the biasing element 220 compressed toward the review configuration. In one embodiment, the lever 264 may include a locking mechanism so that the lever 264 may be locked toward the compressed configuration.

If, during this review configuration, the operator determines that the clip 202 is in the desired position relative to the target tissue, the operator may press the push button 262 using, for example, his/her thumb. The push button 262 is connected to the proximal end of the deployment element 210 so that, when pressed, the deployment element 210 is drawn proximally relative to the endoscope 204 to move the clip 202 distally relative to the cap 208 until the clip 202 is moved distally off the cap 208. If, however, during the review configuration the operator determines that the clip 202 is not in the desired position relative to the target tissue, the operator may release the lever 264, thereby releasing a tension therealong to permit the biasing element 220 to revert to its biased configuration. As the biasing element 220 reverts toward its biased configuration, the biasing element 220 pushes the cap 208 proximally along the endoscope 2-4 from the review configuration toward the insertion configuration so that the clip 202 may be repositioned, as necessary.

Figure 16:
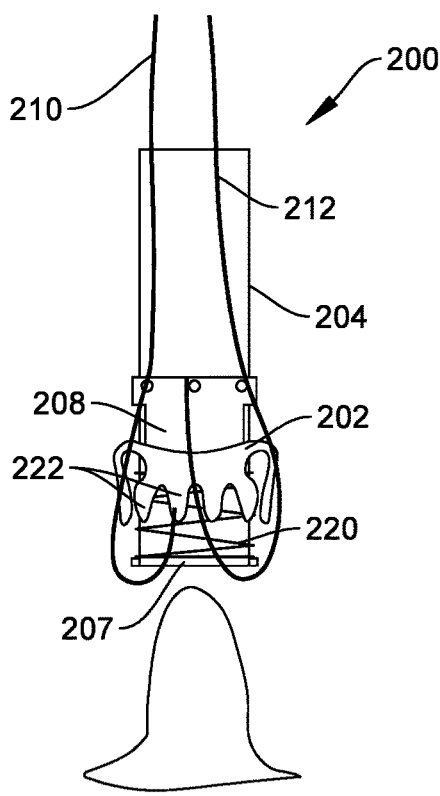
FIG. 16 shows a longitudinal side view of the distal portion of the system of FIG. 11, in an insertion configuration.
Figure 17:
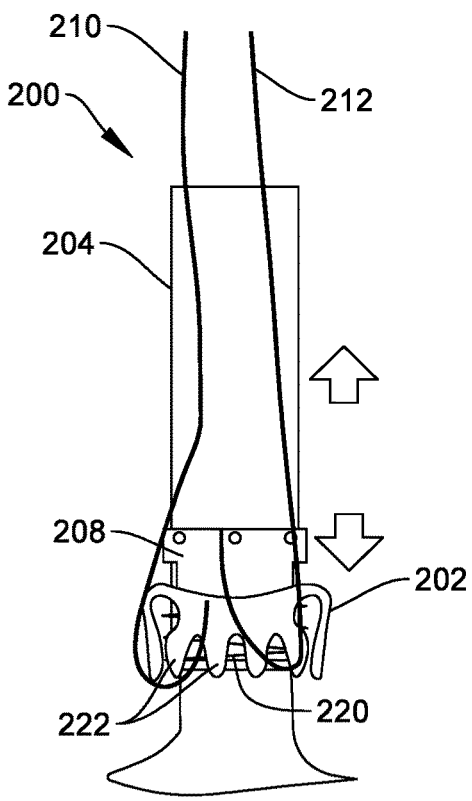
FIG. 17 shows a longitudinal side view of the distal portion of the system of FIG. 11, in a review configuration.

An exemplary method for clipping tissue using the clipping system 200, as shown in FIGS. 16-21, may be substantially similar to the method for clipping tissue using the system 100. Similarly to the system 100, the clip 202, mounted over the distal end 206 of the endoscope 204 via the cap 208 in the insertion configuration, may be inserted through a body lumen (e.g., of a gastrointestinal tract) to a target site within the body. As described above, the cap 208 is biased toward the insertion configuration via the biasing element 220. As shown in FIG. 16, once the clip 202 is positioned over a target tissue, a suction force may be applied through a working channel of the endoscope 204, drawing the tissue therein, between the jaws 214 of the clip 202. The clip 202 may then be moved from the insertion configuration toward the review configuration, as shown in FIG. 17, by moving the repositioning element 212 proximally relative to the endoscope 204 so that the cap 208 is moved distally therealong, thereby compressing the biasing element 220. In the review configuration, teeth 222 may extend distally past the distal-most end 207 of the endoscope 204 so that a position of the teeth 222 relative to the target tissue is visible via the endoscope 204.

Figure 18:
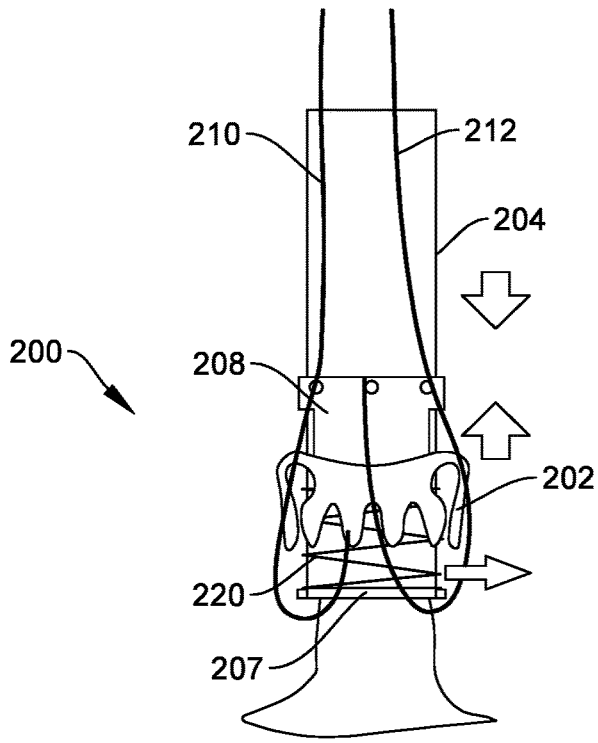
FIG. 18 shows a longitudinal side view of the distal portion of the system of FIG. 11, being moved toward the insertion configuration via a repositioning element.
Figure 19:
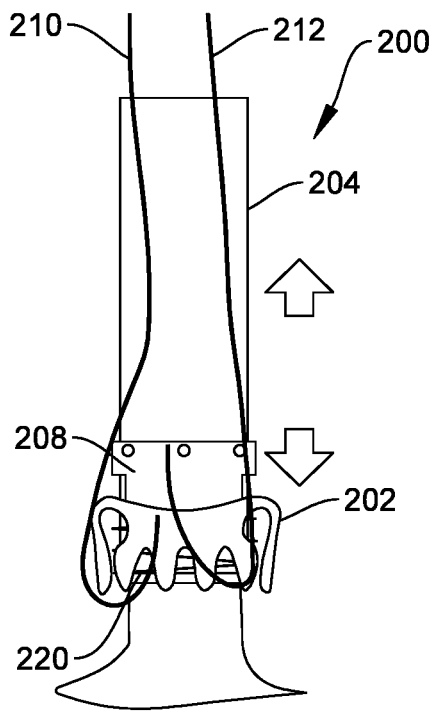
FIG. 19 shows a longitudinal side view of the distal portion of the system of FIG. 11, being moved toward the review configuration.

When the clip 202 is in the review configuration, the operator may determine whether the clip 202 is in the desired position relative to the target tissue. If the clip 202 is not in the desired position, a tension along the repositioning element 212 may be released so that the biasing element 220 may revert toward its biased configuration to move the cap 208 from the review configuration back toward the insertion configuration, as shown in FIG. 18. In the insertion configuration, the clip 202 may be repositioned relative to the target tissue and once again moved toward the review configuration, as shown in FIG. 19. This process may be repeated, as necessary, until the clip 202 is determined to be in the desired position relative to the target tissue.

Figure 20:
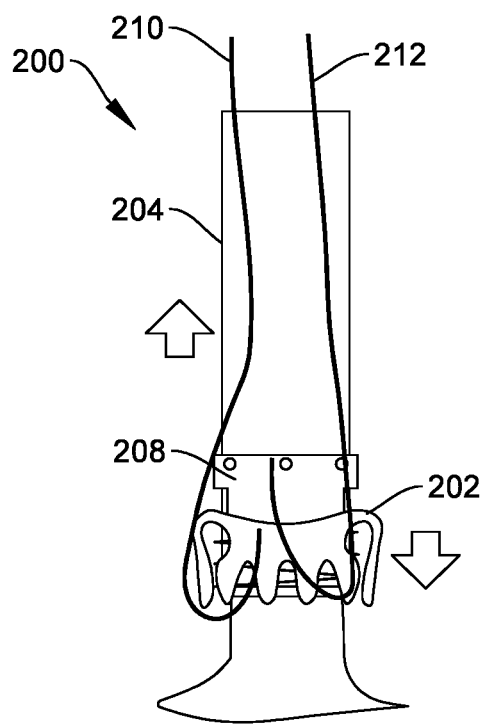
FIG. 20 shows a longitudinal side view of the distal portion of the system of FIG. 11, being moved toward the deployed configuration.
Figure 21:
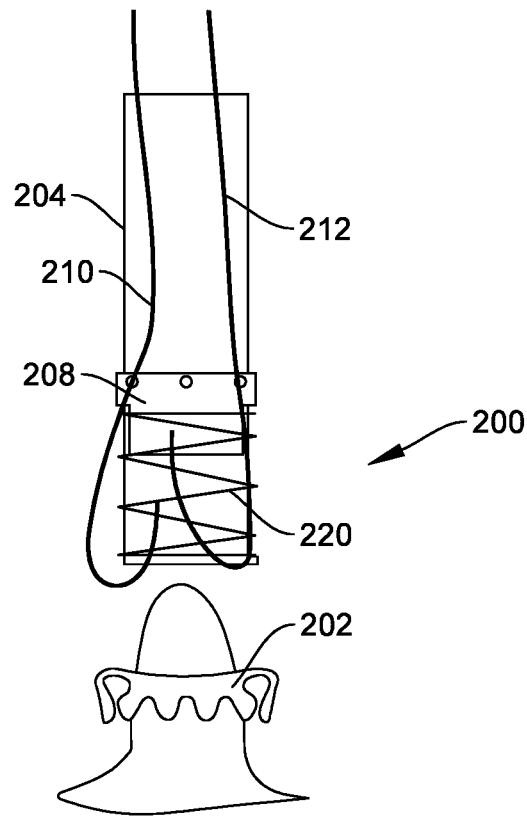
FIG. 21 shows a longitudinal side view of the distal portion of the system of FIG. 11, with a clip deployed in a body clipped over a target tissue.

Once it has been determined that the clip 202 is in the desired position, the clip 202 may be moved toward the deployed configuration by moving the deployment element 210 proximally relative to the endoscope 204, as shown in FIG. 20, until the clip 202 has been pushed distally off of the cap 208, as shown in FIG. 21. As described above, when the clip 202 is pushed distally off the cap 208, the clip 202 is permitted to revert toward its biased closed configuration so that the target tissue is gripped between the jaws 214 thereof. In addition, since the deployment element 210 is no longer crimped between the clip 202 and the cap 208, the distal portion 248 of the deployment element 210 becomes unwinds from the clip 202 so that the knot 246 is disengaged therefrom, releasing the clip 202 in the body, clipped over the target tissue. It will be understood by those of skill in the art, that since the repositioning element 212 is connected to the cap 208 and is in no way connected to the clip 202, the repositioning element 212 need not release or disengage from the cap 208.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:
1. A clipping system for treating tissue, comprising:
a cap configured to be mounted over a distal end of an endoscope, the cap extending longitudinally from a proximal end to a distal end and including a channel extending therethrough so that the cap may be located adjacent to target tissue within a living body;

a clip configured to be mounted over the cap, the clip including first and second jaws movably connected to one another via hinges, at least one of the hinges being biased to draw the first and second jaws toward one another, the clip movable relative to the cap between an insertion configuration, in which the first and second jaws extend over opposing portions of the cap so that the first and second jaws are separated from one another to receive a target tissue therebetween, a review configuration, in which the clip is moved distally relative to the cap so that a portion of the clip extends distally until at least a portion of the clip extends into a field of view of an optical system of the endoscope on which the cap is mounted, and a deployed configuration in which the clip is moved distally off of the clip so that the first and second jaws are drawn toward one another under the bias of the at least one of the hinges to close over tissue received therebetween;

a deployment element extending from a distal end releasably coupled to the clip through the channel of the cap to a proximal end which, in use, remains outside the living body while the cap is adjacent to the target tissue, the deployment element being configured so that a proximal movement of the deployment element relative to the cap moves the clip distally relative to the cap toward the deployed configuration; and a repositioning element extending from a distal end coupled to one of the cap and the clip proximally through the channel of the cap to a proximal end that, in use, remains outside the living body, the repositioning element being configured so that moving the repositioning element proximally relative to the cap moves the clip proximally relative to the cap from the review configuration to the insertion configuration.

2. The system of claim 1, wherein a distal portion of the deployment element is looped about the first jaw of the clip such that a portion of the distal portion of the deployment element is crimped between an interior surface of the cap and an exterior surface of the endoscope on which the cap is mounted, an enlargement at the distal end of the deployment element engaged between adjacent teeth of the first jaw, a remaining length of the deployment element extending proximally from the clip to be received enter a distal opening of the endoscope on which the cap is mounted to extend proximally through a channel of the endoscope.

3. The system of claim 1, wherein the cap is formed of a transparent material and is configured to fit over the distal end of the endoscope via a friction fit so that a proximal portion of the cap extends over the distal end of the endoscope on which the cap is mounted and a distal portion of the cap extends distally past the distal end of the endoscope.

4. The system of claim 3, wherein, in the insertion configuration the clip extends over the proximal portion of the cap and, in the review configuration the clip extends over the distal portion of the cap so that the clip is visible via the optical system of the endoscope on which the cap is mounted through the transparent cap.

5. The system of claim 1, wherein the cap includes a protrusion extending from an exterior surface of the cap, the protrusion configured to engage a portion of the clip when the clip is in the review configuration.

6. The system of claim 1, wherein the distal end of the repositioning element releasably engages the second jaw of the clip, a remaining length of the repositioning element passing through a longitudinal slot extending through the cap to extend proximally through a channel of the endoscope on which the cap is mounted.

7. The system of claim 1, further comprising a biasing element extending between the distal end of the cap and a stop at the distal-most end of the endoscope on which the cap is mounted, the biasing element biasing the cap toward the insertion configuration, in which an entirety of the clip mounted over the cap is proximal of the distal-most end of the endoscope.

8. The system of claim 7, wherein the distal end of the repositioning element is connected to the cap, a remaining length of the cap extending distally between an interior surface of the cap and an exterior surface of the endoscope on which the cap is mounted and passed distally through a distal opening of a channel of the endoscope so that the repositioning element extends proximally through the channel of the endoscope to a proximal end.

9. The system of claim 8, wherein the repositioning element is drawn proximally relative to the endoscope to move the cap distally relative to the endoscope, compressing the biasing element so that the cap and the clip mounted thereon are moved toward the review configuration.

10. The system of claim 9, wherein, in the review configuration, gripping features along the first and the second jaws extend distally past the distal-most end of the endoscope so that the gripping features are in the field of view of the endoscope.

11. A tissue clipping system, comprising:

a transparent cap configured to be mounted over a distal end of an endoscope, the cap extending longitudinally from a proximal end to a distal end and including a channel extending therethrough, the cap including a proximal portion configured to extend over the distal end of the endoscope on which the cap is mounted and a distal portion configured to extend distally past the distal end of the endoscope on which the cap is mounted;

a clip configured to be mounted over the cap, the clip including first and second jaws movably connected to one another via hinges, at least one of the hinges being biased to draw the first and second jaws toward one another, the clip movable relative to the cap between an insertion configuration, in which the first and second jaws extend over opposing portions along the proximal portion of the cap so that the first and second jaws are separated from one another to receive target tissue therebetween, a review configuration, in which the clip is moved distally relative to the cap so that the clip extends over the distal portion of the cap to a position configured to be within a field of view of an optical system of the endoscope on which the cap is mounted, and a deployed configuration, in which the clip is moved distally off of the clip so that the first and second jaws are drawn toward one another under the bias of the at least one of the hinges;

a deployment element releasably coupled to the clip so that, when the deployment element is drawn proximally relative to the cap via a first distance, the clip is moved from the insertion configuration toward the review configuration, and when the deployment element is drawn further proximally relative to the cap a second distance, the clip is moved from the review configuration toward the deployed configuration; and a repositioning element releasably coupled to the clip so that, when it is desired to reposition the clip relative to a target tissue, the repositioning element is drawn proximally relative to the cap to move the clip from the review configuration toward the insertion configuration.

12. The system of claim 11, wherein a distal portion of the deployment element is looped about the first jaw of the clip such that a portion of the distal portion of the deployment element is crimped between an interior surface of the cap and an exterior surface of the endoscope on which the cap is mounted and an enlargement at the distal end of the deployment element being is engaged between adjacent teeth of the first jaw, a remaining length of the deployment element extending proximally from the clip to be received within a distal opening of the endoscope on which the cap is mounted to extend proximally through a channel of the endoscope.

13. The system of claim 12, wherein, when the clip is moved distally of the cap in the deployed configuration, the distal portion of the deployment element becomes unwound from the first jaw such that the enlargement is disengaged from the clip and the clip is released from the deployment element to remain closed over the target tissue.

14. The system of claim 11, wherein the distal end of the repositioning element releasably engages the second jaw of the clip, a remaining length of the repositioning element passing through a longitudinal slot extending through the cap.

15. The system of claim 11, wherein the cap includes a protrusion extending from an exterior surface of the cap, the protrusion configured to engage a portion of the clip when the clip is in the review configuration.

\* \* \* \* \*